United States Patent [19]

Fisher

[11] Patent Number: 5,412,108
[45] Date of Patent: May 2, 1995

[54] METHOD FOR PREPARING 1,2,4-CYCLOHEXANETRICARBOXYLIC ACID AND ANHYDRIDE

[75] Inventor: Allison M. Fisher, Aurora, Ill.

[73] Assignee: Amoco Corporation, Chicago, Ill.

[21] Appl. No.: 177,661

[22] Filed: Jan. 5, 1994

[51] Int. Cl.6 .................... C07D 407/00; C07C 61/09
[52] U.S. Cl. ..................................... 549/245; 562/509
[58] Field of Search ......................... 549/245; 562/509

[56] References Cited

U.S. PATENT DOCUMENTS

| | | |
|---|---|---|
| 3,444,237 | 5/1969 | Jaffe ..................................... 562/509 |
| 4,754,064 | 6/1988 | Lillwitz .............................. 562/509 |
| 5,202,475 | 4/1993 | Cook et al. .......................... 562/509 |
| 5,278,339 | 1/1994 | Cook ................................... 562/509 |
| 5,286,903 | 2/1994 | Irick, Jr. et al. .................... 562/509 |

FOREIGN PATENT DOCUMENTS 49052897 5/1974 Japan .

OTHER PUBLICATIONS

Kemp et al. J. Org. Chem 1981, 46, 5140–5143.
Steitz, The Journal of Organic Chem. 1968 pp. 2978–2979.
Stack et al, J. Am. Chem. Soc. 1991, 113, 5918–20.
Chemical Abstract CA 101:236240h (1983).
Freifelder et al., "Low–Pressure Hydrogenation of Some Benzenepolycarboxylic Acids with Rhodium Catalyst," Oct. 1966, Journal of Organic Chemistry, vol. 31, pp. 3438–3439.

*Primary Examiner*—Cecilia Tsang
*Attorney, Agent, or Firm*—Thomas E. Nemo; Wallace L. Oliver

[57] ABSTRACT

A method for preparing cis, cis, cis-1,2,4-cyclohexanetricarboxylic acid comprising contacting trimellitic acid with molecular hydrogen at an elevated temperature and pressure in the presence of a solvent and a catalyst comprising a transition metal deposited on a carbon support having a surface area of at least about 940 $m^2$/gram, and the anhydride formed by dehydrating cis, cis, cis-1,2,4-cyclohexanetricarboxylic acid.

4 Claims, No Drawings

METHOD FOR PREPARING 1,2,4-CYCLOHEXANETRICARBOXYLIC ACID AND ANHYDRIDE

FIELD OF THE INVENTION

This invention relates to an improved method for preparing 1,2,4-cyclohexanetricarboxylic acid. More particularly, this invention relates to an improved method for preparing 1,2,4-cyclohexanetricarboxylic acid by the hydrogenation of trimellitic acid using a catalyst comprising a transition metal deposited on a high surface area carbon support and wherein the 1,2,4-cyclohexanetricarboxylic acid produced is primarily the cis, cis, cis isomer. This invention also relates to the hexahydrotrimellitic anhydride formed by dehydrating cis, cis, cis-1,2,4-cyclohexanetricarboxylic acid.

BACKGROUND OF THE INVENTION 1,2,4-Cyclohexanetricarboxylic acid (CHTA) is a useful organic compound. For example, CHTA can be reacted with one or more aliphatic or aromatic alcohols to prepare the triesters of CHTA. These triesters, particularly those prepared from aliphatic alcohols having 4 to 10 carbon atoms, are useful as synthetic lubricants and as plasticizers. Additionally, CHTA can be reacted with di- or polyfunctional amines such as, 1,6-diaminohexane, to form polymeric amide/imide compounds. When CHTA is reacted with di- or polyamines to form polyamides or polyamide/imides, water is produced during the polymerization reaction. However, by using the anhydride of CHTA, less water is generated during the polymerization reaction allowing for a more efficient, more easily conducted polymerization reaction.

Prior methods for preparing CHTA involved the hydrogenation of the alkali metal or ammonium salt of trimellitic acid, which resulted in the salt of CHTA. In order to form the desired CHTA, the salt required neutralization to the triacid. It would, however, be desirable to produce CHTA directly from trimellitic acid without the use of a salt and the subsequent neutralization step. The present invention provides such an improved method.

SUMMARY OF THE INVENTION

A method for preparing 1,2,4-cyclohexanetricarboxylic acid comprising contacting trimellitic acid with molecular hydrogen at an elevated temperature and pressure in the presence of a solvent and a catalyst comprising a transition metal deposited on a carbon support having a surface area of at least about 940 m$^2$/gram.

The method disclosed herein produces 1,2,4-cyclohexanetricarboxylic acid that is substantially cis, cis, cis-1,2,4-cyclohexanetricarboxylic acid, i.e., each of the three carboxylic acid moleties on the cyclohexanetricarboxylic acid molecule are on the same side of the cyclohexane ring structure in the 1,2,4-cyclohexanetricarboxylic acid molecule. Also, the cis, cis, cis-1,2,4-cyclohexanetricarboxylic acid produced by the method of this invention can be dehydrated to form the corresponding anhydride, which anhydride is useful for preparing polymeric molecules such as polyamide/imides by the reaction of the anhydride with di- or polyfunctional amines such as 1,6-diaminohexane, oxybisaniline, 1,4-diaminobenzene, and the like. Since the anhydride of cis, cis, cis-1,2,4-cyclohexanetricarboxylic acid is a single isomer, it is more easily purified compared to a mixture of anhydride isomers.

DETAILED DESCRIPTION OF THE INVENTION 1,2,4-Cyclohexanetricarboxylic acid can be efficiently prepared directly from trimellitic acid by the hydrogenation of trimellitic acid in a solvent, using molecular hydrogen as the source of hydrogen and a hydrogenation catalyst comprising a transition metal deposited on a carbon support, wherein the carbon support has a surface area of at least about 940 square meters per gram (m$^2$/gram). When the surface area was below this amount, the hydrogenation reaction was found not to proceed. In addition, the 1,2,4-cyclohexanetricarboxylic acid produced by the method of this invention using a high surface area catalyst is mostly in the cis, cis, cis- form, i.e. where the carboxylic acid moleties are on the same side of the cyclohexane ring.

Trimellitic acid, the starting material, is easily prepared by hydrolyzing trimellitic anhydride. Trimellitic anhydride is available from Amoco Chemical Company, Chicago, Ill.

In the method of this invention, the trimellitic acid is contacted with a suitable hydrogenation solvent and subjected to hydrogenation using molecular hydrogen, a catalyst, and a reaction temperature and pressure sufficient to hydrogenate the aromatic ring. Suitable solvents include polar solvents such as water, one or more low molecular weight aliphatic carboxylic acids such as acetic acid, having about 1 to about 10 carbon atoms, for example acetic acid or propronic acid, one or more low molecular weight ethers preferably having 2 to about 20 carbon atoms such as diethylether, methylethylether, tetrahydrofuran, and the like, one or more esters, preferably having 3 to about 20 carbon atoms such as methyl-, ethyl-, or propyl acetate and one or more ketones, preferably having 3 to about 20 carbon atoms, such as acetone or methylethyl ketone. It is preferable to use a solvent that will at least partially, and more preferably, completely dissolve the trimellitic acid starting material and the 1,2,4-cyclohexanetricarboxylic acid product at the reaction temperature used for the hydrogenation reaction. Preferably, the solvent for the hydrogenation reaction is water or a mixture of water with one or more low molecular weight aliphatic carboxylic acids, or a mixture of water with a miscible aliphatic ether such as tetrahyrofuran. When a miscible ether is used with water, the mixture is about 20 to 80 volume percent ether.

The amount of solvent used for the hydrogenation of trimellitic acid to 1,2,4-cyclohexanetricarboxylic acid is preferably an amount that at least partially dissolves the trimellitic acid at the reaction temperature used for the hydrogenation reaction. The amount of solvent is preferably at least about 5 milliliters of solvent per gram of trimellitic acid, more preferably, at least about 15 milliliters of solvent per gram of trimellitic acid. When water is used as the reaction solvent, or as part of the reaction solvent, trimellitic anhydride can be used as the starting material since it hydrolyzes at the hydrogenation reaction conditions to form trimellitic acid. It is not necessary for all of the trimellitic acid starting material or all of the 1,2,4-cyclohexanetricarboxylic acid to be dissolved in the solvent during the hydrogenation reaction.

The temperature used for the hydrogenation of trimellitic acid to 1,2,4-cyclohexanetricarboxylic acid is a temperature that provides for the hydrogenation of the aromatic ring in the trimellitic acid molecule to a cyclohexane ring substituted with the three carboxylic acid moieties. A suitable reaction temperature is at least about 25° C., preferably at least about 50° C. Preferably, the reaction temperature is not greater than about 200° C., more preferably, not greater than about 150° C. The reaction pressure for the hydrogenation of trimellitic acid to 1,2,4-cyclohexanetricarboxylic acid is a pressure that provides for the hydrogenation of the aromatic ring in the trimellitic acid molecule. Preferably, the reaction pressure is at least about 20 psig, more preferably at least about 1000 psig. Most preferably, the reaction pressure is not greater than about 2500 psig, more preferably not more than about 2000 psig.

In the method of this invention, molecular hydrogen is used to hydrogenate the trimellitic acid to 1,2,4-cyclohexanetricarboxylic acid. The molecular hydrogen can be introduced into the reaction zone as pure or substantially pure molecular hydrogen. It can also be introduced as a mixture with an inert gas diluent such as nitrogen or helium. Most preferably, undiluted pure, or substantial pure, molecular hydrogen is used for the hydrogenation reaction. Any suitable reaction vessel can be used for the hydrogenation reaction, preferably one that is constructed of a material that is inert to the reaction mixture.

The hydrogenation catalyst used in the method of this invention comprises a transition metal deposited on a high surface area carbon support. The surface area of the carbon support must be at least about 940 square meters per gram (m²/g) of carbon support, more preferably at least about 1000 m²/g of carbon support. When the surface area of the carbon support is below this amount the hydrogenation reaction is ineffective. The transition metal can be deposited on the carbon support by methods known in the art. The transition metal is suitably selected from platinum, palladium, rhodium, ruthenium, nickel, iridium, and rhenium, or a mixture of one or more thereof. Preferably, the transition metal is one or more of platinum, palladium, rhodium or ruthenium. Most preferably, the transition metal is rhodium. The amount of metal on the carbon support is suitably about 0.5 weight percent to about 20 weight percent, preferably about 1 weight percent to about 10 weight percent of the total catalyst. A suitable catalyst is 5% rhodium on CP-56 carbon available from Engelhard Corporation, Islin, N.J. The surface area of the carbon support materials referred to hereinabove can be measured by the BET (Brunauer, Emmett and Teller) procedure. The amount of catalyst used for the hydrogenation of trimellitic acid to 1,2,4-cyclohexanetricarboxylic acid is an amount that provides for the hydrogenation of the trimellitic acid. Preferably, the amount of catalyst used is about 0.005 to about 0.5 grams of catalyst, more preferably about 0.1 to about 0.25 grams of catalyst, per gram of trimellitic acid.

The hydrogenation catalyst can be added to the reaction mixture in particulate form and can be present in the reaction mixture as a slurry. Alternatively, the reaction mixture containing the trimellitic acid and solvent can be passed or percolated through a fixed bed of the hydrogenation catalyst. When a fixed bed of the catalyst is used, it is preferable for the trimellitic acid starting material and 1,2,4-cyclohexanetricarboxylic acid product to be completely dissolved in the reaction solvent.

Subsequent to the hydrogenation of trimellitic acid to cis, cis, cis1,2,4-cyclohexanetricarboxylic acid, the high surface area catalyst can be washed with a polar solvent such as an ether, for example, an ether having 2 to about 10 carbon atoms; an ester, for example, an ester having about 3 to about 10 carbon atoms; an aliphatic carboxylic acid, for example, an acid having about 2 to about 10 carbon atoms; a ketone, for example, a ketone having 3 to about 10 carbon atoms; or a mixture of one or more of such solvents. Low molecular weight aromatic compounds such as benzene, toluene and xylene are also useful for washing the catalyst. The washing removes impurities and allows for the catalyst to be used repeatedly as a catalyst for hydrogenating trimellitic acid to cis, cis, cis-1,2,4-cyclohexanetricarboxylic acid. The washing can be completed by adding solvent to the catalyst while the catalyst is on a filter or centrifuge. Alternatively, the used catalyst can be suspended, preferably with agitation, in the solvent, then separated from the solvent. Preferably, the catalyst is washed twice, more preferably at least four times, preferably using at least about 2, more preferably using at least about 5 grams of solvent per gram of catalyst, per wash. The washing can be done at ambient or at elevated temperatures.

The 1,2,4-cyclohexanetricarboxylic acid prepared by the method of this invention is mostly the cis isomer, i.e. the three carboxylic acid groups are on the same side of the cyclohexane ring. In the method of this invention, the direct, unpurified product is at least about 75% cis isomer, preferably at least about 85% of the 1,2,4-cyclohexanetricarboxylic acid produced is the cis-isomer, i.e. where all three of the carboxylic acid moieties are on the same side of the cyclohexane ring. The structure of such cis, cis, cis- 1,2,4-cyclohexanetricarboxylic acid is shown as structure (I) below, which structure was confirmed by x-ray crystallographic analysis.

The 1,2,4-cyclohexanetricarboxylic acid product mixture formed by the method of this invention can be purified by recrystallization from a suitable solvent to prepare substantially pure cis, cis, cis-1,2,4-cyclohexanetricarboxylic acid. Suitable recrystallization solvents include tetrahydrofuran (THF) and acetonitrile (CH$_3$CN) or mixtures thereof.

The cis, cis, cis- 1,2,4-cyclohexanetricarboxylic acid prepared by the method of this invention can be converted to the corresponding anhydride by dehydrating the cis, cis, cis- 1,2,4-cyclohexanetricarboxylic acid. The dehydration is suitably conducted by reacting the cis, cis, cis1,2,4-cyclohexanetricarboxylic acid with a dehydrating agent such as acetic anhydride, trifluoroacetic anhydride, methoxyacetylene, phosphorus pentoxide, dicyclohexylcarbodiimide, and the like. The resulting anhydride has a melting point of 154°–156° C., and has the structure (II) shown below. In structures (I) and (II) below, the cyclohexane ring is in the plane of the page and the heavy lines represent carbon-carbon bonds extending up and out of the plane of the page.

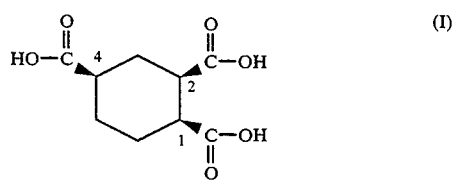

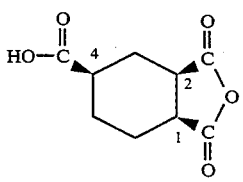

Because the hydrogenation reaction disclosed herein produces primarily the cis, cis, cis-isomer of 1,2,4-cyclohexanetricarboxylic acid, the method of this invention can be used to readily prepare anhydride (II) having a purity of at least about 95%, more preferably at least about 98%, and most preferably at least about 99% as a single isomer. The anhydride (II) can be purified by, for example, recrystallization from a suitable solvent. As described hereinabove, the anhydride (II) is useful for preparing esters by the reaction of the anhydride with alcohols, such as aliphatic primary alcohols having 4 to 10 carbon atoms. These esters are useful as synthetic lubricants and as plasticizers for polymeric materials. The anhydride (II) can also be condensed with one or more di- or polyamines such as 1,6-hexanediamine, 1,4-diaminobenzene, oxybisaniline, 4,4'-diaminobiphenyl and the like, to form polyamide or polyamide/imide materials.

The hydrogenation of trimellitic acid according to the method disclosed herein can be conducted in the batch or continuous mode.

The invention will be illustrated by reference to the following specific examples. However, these examples are not intended to limit the scope of the invention.

Example 1: Synthesis of 1,2,4-Cyclohexanetricarboxylic Acid (CHTA).

Trimellitic acid (100 g) was dissolved in a mixture of tetrahydrofuran (THF) and water (1:1 by volume, 1.2 liter) and 5% Rh/Carbon catalyst on CP-56 carbon, surface area (BET) of 1000 m²/gram, obtained from Engelhard Corporation (20 grams) was added. The slurry was placed in a glass-lined stainless steel autoclave. The autoclave was purged twice with nitrogen, then pressurized to approximately 1000 psig with hydrogen. The autoclave was heated to about 45° C., and pressurized to 1400 psig. The temperature of the autoclave was raised to 60° C. and stirred at 1000 rpm for four hours. The reaction mixture was allowed to cool, the autoclave vented and the contents removed. The slurry was filtered using suction through a medium porosity glass fritted Buchner funnel and the catalyst was rinsed well the THF: water (1:1) mixture. After concentrating and drying the filtrate, 1,2,4-CHTA, was isolated as an off-white crystalline solid (quantitative recovery).

Approximately 10 mg of crude product was silylated with bis(trifluoromethyl)silyltrifluoroacetamide at 80° C. and analyzed by gas chromatography (GC). Selectivity to a single isomer of CHTA was approximately 90% (uncorrected).

The crude product was dissolved in hot THF (200 ml) and acetonitrile ($CH_3CN$) (900 ml) was added. The pale yellow solution was concentrated to ca. 800 ml on a hot plate, filtered (hot, gravity) and allowed to cool. White, crystalline 1,2,4-CHTA was isolated (73 g, mp 181°–183° C.) by filtering (suction), and rinsed with fresh $CH_3CN$. Analysis of the product by gas chromatography as described above indicated a purity of 98+% (uncorrected).

Analysis of the product by proton nuclear magnetic resonance spectroscopy resulted in the following spectrum relative to tetramethylsilane (TMS):

| δ ppm (TMS) | Description of Absorption | Relative number of Protons by Integration |
| --- | --- | --- |
| 12.15 | broad singlet | 3 |
| 3.01 | multiplet | 1 |
| 2.44 | multiplet | 1 |
| 2.24 | multiplet | 1 |
| 2.07 | multiplet | 2 |
| 1.76 | multiplet | 2 |
| 1.48 | multiplet | 1 |
| 1.08 | multiplet | 1 |

Analysis by infrared spectroscopy using a potassium bromide pellet resulted in a spectrum having absorbances at $\nu$ 3232, 1708 and 1196 $cm^{-1}$.

Analysis by x-ray crystallography confirmed the structure of the product as that of compound (I) shown hereinabove where the carboxylic acid group at $C_1$, was axial and the carboxylic acid groups at $C_2$ and $C_4$ were equatorial.

Example 2: When a procedure for hydrogenating trimellitic acid similar to Example 1 was run using a 5% rhodium on carbon catalyst having a surface area of 935 m²/gram (5% rhodium on CP-97 carbon from Engelhard Corporation) the hydrogenation to 1,2,4-cyclohexanetricarboxylic acid did not occur.

Example 3: Synthesis of the anhydride of cis, cis, cis-1,2,4-cyclohexanenetricarboxylic Acid.

1,2,4-Cyclohexanetricarboxylic acid (300 grams, 1.39 moles) prepared as in Example 1, was dissolved in anhydrous THF (1.5 liters) under nitrogen at room temperature, with stirring. Acetic anhydride (144 ml, 1.53 moles) was added and the solution allowed to stir overnight. The reaction mixture was concentrated on a rotary evaporator to remove the THF solvent, and toluene was added to precipitate the hexahydrotrimellitic anhydride. The resulting slurry cooled to room temperature under nitrogen, filtered (suction) and rinsed with fresh toluene. The white, crystalline product (243 g. 88% yield) was dried at 50° C. under vacuum (ca. 0.1 torr) and had a mp of 154°–156° C. Analysis by gas chromatography as described above indicated a purity of 98+% (uncorrected). Analysis of the product by proton nuclear magnetic resonance spectroscopy resulted in the following spectrum relative to tetramethylsilane (TMS):

| δ ppm (TMS) | Description of Absorption | Relative number of Protons by Integration |
| --- | --- | --- |
| 3.51 | multiplet | 1 |
| 3.26 | multiplet | 1 |
| 2.32 | multiplet | 1 |
| 2.16 | multiplet | 1 |
| 2.01 | multiplet | 1 |
| 1.82 | multiplet | 1 |
| 1.70 | multiplet | 1 |
| 1.45 | multiplet | 1 |
| 1.26 | multiplet | 1 |

Analysis by Carbon 13 nuclear magnetic resonance spectroscopy resulted in the following absorptions (δ) 175.29, 173.99, 173.31, 38.94, 38.87, 37.87, 26.99, 24.27 and 20.13 ppm.

Analysis by infrared spectroscopy using a potassium bromide pellet resulted in a spectrum having absorbances at $\upsilon$3041-2620, 1857, 1788, 1705, 1436, 1236 and 900 cm$^{-1}$.

Having described the invention, that which is claimed is:

1. The anhydride of cis, cis, cis- 1,2,4-cyclohexanetricarboxylic acid having the structure

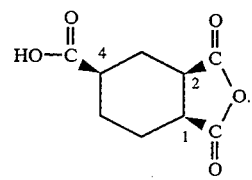

2. The anhydride of claim 1 having a purity of at least about 98%.

3. A method for preparing the anhydride of cis, cis, cis-1,2,4-cyclohexanetricarboxylic acid comprising dehydrating cis, cis, cis-1,2,4-cyclohexanetricarboxylic acid with a dehydrating agent.

4. A method for preparing 1,2,4-cyclohexanetricarboxylic acid comprising contacting trimellitic acid with molecular hydrogen at an elevated temperature and pressure in the presence of a solvent and a catalyst comprising a transition metal deposited on a carbon support having a surface area of at least about 940 square meters per gram.

* * * * *

UNITED STATES PATENT AND TRADEMARK OFFICE
CERTIFICATE OF CORRECTION

PATENT NO.: 5,412,108

DATED: May 2, 1995

INVENTOR(S): Allison M. Fisher

It is certified that error appears in the above-identified patent and that said Letters Patent is hereby corrected as shown below:

| Col. | Line |  |
|------|------|---|
| 1 | 57 | "three carboxylic acid moleties" should read --three carboxylic acid moieties-- |
| 2 | 18-19 | "carboxylic acid moleties" should read --carboxylic acid moieties-- |
| 3 | 5-6 | "carboxylic acid moleties" should read --carboxylic acid moieties-- |
| 4 | 35 | "carboxylic acid moleties" should read --carboxylic acid moieties-- |

Signed and Sealed this

Thirtieth Day of January, 1996

Attest:

BRUCE LEHMAN

Attesting Officer

Commissioner of Patents and Trademarks